(12) United States Patent
Behnk (10) Patent No.: US 11,278,903 B2
(45) Date of Patent: Mar. 22, 2022

(54) TEST CELL AND MEASURING METHOD

(71) Applicant: Holger Behnk, Hamburg (DE)

(72) Inventor: Holger Behnk, Hamburg (DE)

( * ) Notice: Subject to any disclaimer, the term of this patent is extended or adjusted under 35 U.S.C. 154(b) by 415 days.

(21) Appl. No.: 16/060,434

(22) PCT Filed: Nov. 16, 2016

(86) PCT No.: PCT/EP2016/077797
§ 371 (c)(1),
(2) Date: Jun. 8, 2018

(87) PCT Pub. No.: WO2017/097553
PCT Pub. Date: Jun. 15, 2017

(65) Prior Publication Data
US 2018/0369806 A1 Dec. 27, 2018

(30) Foreign Application Priority Data
Dec. 10, 2015 (EP) .................................. 15199277

(51) Int. Cl.
*B01L 3/00* (2006.01)
*B01F 13/08* (2006.01)
*B01F 13/10* (2006.01)
*G01N 21/03* (2006.01)
(Continued)

(52) U.S. Cl.
CPC ........ *B01L 3/5085* (2013.01); *B01F 13/0818* (2013.01); *B01F 13/1022* (2013.01);
(Continued)

(58) Field of Classification Search
CPC .................. B01L 3/5085; B01L 3/508; B01L 2200/0647; B01L 2300/0609;
(Continued)

(56) References Cited

U.S. PATENT DOCUMENTS 4,918,984 A   4/1990  Martinoli et al.
6,117,398 A * 9/2000  Bienhaus ........... C12N 15/1013
                                                       209/215
(Continued)

FOREIGN PATENT DOCUMENTS

EP           1681564 B1      5/2009
WO     WO 2004/040271   *    5/2004

OTHER PUBLICATIONS

International Search Report dated Dec. 23, 2016 (PCT/EP2016/077797).

*Primary Examiner* — Benjamin R Whatley
*Assistant Examiner* — Jacqueline Brazin
(74) *Attorney, Agent, or Firm* — Alix, Yale & Ristas, LLP (57) ABSTRACT

The invention relates to a test cell for mixing a liquid. The test cell comprises an interior space for receiving the liquid and a running rail, which is formed in the interior space, for a ball, wherein the running rail is formed by two projections which project into the interior space from opposite side walls of the test cell. According to the invention, the running rail has a straight section and is deflected upward at both ends. In the test cell according to the invention, a high filling level can be achieved with a low quantity of liquid, this being advantageous for optical measurements. The invention also relates to a measuring method using the test cell.

14 Claims, 5 Drawing Sheets

(51) Int. Cl.
*G01N 33/49* (2006.01)
*G01N 21/59* (2006.01)

(52) U.S. Cl.
CPC .............. *B01L 3/508* (2013.01); *G01N 21/03* (2013.01); *B01L 2200/0647* (2013.01); *B01L 2300/0609* (2013.01); *B01L 2300/0858* (2013.01); *G01N 21/59* (2013.01); *G01N 33/4905* (2013.01); *G01N 2021/0378* (2013.01); *G01N 2021/0382* (2013.01)

(58) Field of Classification Search
CPC .......... B01L 2300/0858; B01F 13/0818; B01F 13/1022; G01N 21/03; G01N 21/59; G01N 33/4905; G01N 2021/0378
USPC ........................................................ 422/547
See application file for complete search history.

(56) References Cited

U.S. PATENT DOCUMENTS

| | | | |
|---|---|---|---|
| 6,767,511 B1 * | 7/2004 | Rousseau | G01N 11/16 422/62 |
| 7,507,377 B2 * | 3/2009 | Rousseau | G01N 35/026 422/534 |
| 7,943,100 B2 * | 5/2011 | Rousseau | G01N 35/025 422/401 |
| 10,605,801 B2 * | 3/2020 | Rousseau | G01N 11/16 |
| 2002/0182110 A1 * | 12/2002 | Behnk | B01L 3/502 422/72 |
| 2009/0117005 A1 * | 5/2009 | Rousseau | B01L 3/50855 422/64 |
| 2010/0143195 A1 | 6/2010 | Gelin | |

* cited by examiner

TEST CELL AND MEASURING METHOD

The invention relates to a cuvette which is suitable for stirring a liquid. The cuvette has an inner space for receiving the liquid. A running rail for a ball is formed in the inner space, wherein the running rail is formed by two projections which project into the inner space from opposite walls of the cuvette. The invention also relates to an associated method.

A liquid in a cuvette can be stirred by a ball being moved within the liquid. By way of the running rail in the inner space of the cuvette, it is possible for a defined path, along which the ball moves during the stirring, to be predefined.

For certain applications, it is desirable to achieve a high fill level in the cuvette with a small quantity of liquid. This applies for example if it is sought to perform an analysis in which light is directed through the liquid. Cuvettes with a running rail usually have a relatively large cross section. Consequently, a relatively large quantity of liquid is required in order to achieve a particular fill level.

SUMMARY OF THE INVENTION

The invention is based on the object of proposing a cuvette which is suitable for stirring a liquid and in the case of which a large fill height is achieved with a small quantity of liquid. Proceeding from the stated prior art, the object is achieved by way of the features of claim 1. Advantageous embodiments are specified in the dependent claims.

According to the invention, the running rail has a rectilinear portion and is deflected upward at both ends.

By virtue of the fact that the running rail is formed by projections which project into the inner space from opposite walls of the cuvette, it becomes possible to keep the cuvette narrow. The ball can thus be guided on the running rail along a defined path, even though the distance between the opposite walls is barely larger than the diameter of the ball.

The running rail may have a portion within which it extends in a rectilinear manner. The running rail may be deflected upward at both ends. Such a deflection upward makes it possible to prevent the situation in which the ball strikes the end wall of the cuvette and, in this way, a high pressure is exerted locally on the liquid.

The invention is based on the realization that effective mixing of the liquid becomes possible by way of movement of the ball along a rectilinear portion and deflection upward. The liquid can in each case be forced outward by the ball, move upward there and, in an upper region of the liquid, return to the center. The described stirring movements result in complete and uniform mixing of the liquid.

If the ball rolls on the bottom of the cuvette, the liquid is subjected to considerable pressure forces. This is undesirable in the case of sensitive liquids. The running rail is therefore preferably arranged such that the ball which rolls on the running rail does not touch the bottom of the cuvette. For mixing of the liquid which is as complete and uniform as possible, it is an advantage if the ball is spaced apart from the bottom of the inner space by only a small distance.

In one preferred embodiment, the cuvette is therefore formed such that an imaginary first circle, which is aligned perpendicularly with respect to the running rail and which touches the bottom of the inner space and two opposite side walls of the inner space, intersects the two projections. More preferably, a smaller, concentric imaginary second circle does not intersect the projections. The diameter of the second circle is at least 50%, preferably at least 60%, more preferably at least 80%, of the diameter of the first circle.

Considerable pressure can act on the liquid at positions where the ball bears on the running rail. In order to keep the adverse effect on the liquid low, the running rail is therefore preferably formed such that the contact region between the running rail and the ball is small. In particular, the projection may be formed such that it has, as viewed in cross section, a convex form in the contact region. The projection may extend as a closed form from the contact region as far as the bottom of the cuvette. Consequently, undercuts, beneath which the liquid can enter, are avoided.

The two projections may be aligned parallel to one another, resulting in a running rail of constant width. The running rail may have a portion within which it extends parallel to the bottom of the cuvette. The transition point between a substantially horizontal portion of the running rail and the upwardly deflected portion is preferably rounded so that the ball is slowed down gently.

The side walls of the cuvette may be substantially parallel to one another. The side walls are those walls on which the projections of the running rail are formed. "Substantially parallel" means that the side walls are aligned parallel to one another in relation to the horizontal dimension, whereas a slight widening upward is permissible in the vertical dimension. It is possible that the side walls are also aligned parallel to one another in the vertical dimension. Tests have shown that it is favorable for the mixing process if the side surfaces diverge slightly in the upward direction. For example, the side surfaces may include an angle of between 0.2° and 5°, preferably of between 0.5° and 2°, in the vertical dimension. All directional specifications are based on the state in which the cuvette stands upright, via its bottom surface, on a horizontal underlying surface.

For optical measurements in which a light beam passes through the two side surfaces and the liquid arranged in the inner space, it is an advantage for the path of the light beam through the cuvette to be short. The distance between the outer side of the first side wall and the outer side of the second side wall is preferably less than 8 mm, more preferably less than 6 mm, more preferably still less than 5 mm. The wall thickness of the cuvette in the region of the side wall is preferably less than 1.5 mm, more preferably less than 1.2 mm, more preferably still less than 0.9 mm. Parallel to the side surface, the inner space of the cuvette may extend for example over 8 mm to 15 mm. The inner space of the cuvette may have a height of between 20 mm and 30 mm.

In order that the light is influenced as little as possible when passing through the side wall, it is possible for the side wall to have a planar portion. The planar portion preferably extends over at least 50%, more preferably over at least 60%, more preferably still over at least 80%, of the entire surface which the cuvette spans in the plane of the side walls.

In order to make optical measurements possible, the cuvette preferably consists of a transparent material, preferably a transparent plastic. For example, the cuvette may consist of polystyrene. The cuvette may be produced as an integral injection-molded part.

The invention also relates to an arrangement composed of a plurality of cuvettes of said type. The cuvettes may be arranged one behind the other in the longitudinal direction spanned by the side walls. The cuvette arrangement may be provided with a guiding device which is aligned in the longitudinal direction, with the result that the arrangement can be positioned along the guiding device such that a light beam is, in a fixed position, able to pass through a specific cuvette. The guiding device may comprise a rib, preferably two ribs, which extend in the longitudinal direction of the cuvette arrangement. The ribs may be formed on the bottom of the cuvette arrangement. The arrangement of cuvettes may be produced as an integral injection-molded part.

The invention also relates to a system composed of a cuvette and of a ball. The ball preferably consists of a magnetic material, with the result that it is able to be moved along the running rail by a magnet, arranged outside the cuvette, in order to mix the liquid. For example, the ball may consist of VA steel.

The diameter of the ball is preferably such that the distance between the ball and the bottom of the cuvette differs by no more than 50%, preferably by no more than 20%, more preferably by no more than 10%, from the distance between the ball and the side wall of the cuvette when the ball bears on the running rail in the center of the cuvette. In one preferred embodiment, the two distances are equal. The running rail of the cuvette may be formed such that the distances in question remain constant when the ball moves along the running rail. The distance between the ball and the bottom of the cuvette is preferably less than 50%, more preferably less than 20%, more preferably still less than 10%, of the diameter of the ball. In an arrangement composed of a plurality of cuvettes, such a ball is preferably provided for each of the cuvettes.

The invention also relates to a system composed of a measurement device and of a cuvette of said type. A filling element of the measurement device is configured to introduce a quantity of liquid into the cuvette. The measurement device furthermore comprises a drive for the ball, which drive is configured to set the ball in motion for the purpose of mixing a liquid contained in the cuvette. The drive is able to drive the ball such that the movement of the ball is deflected upward at the end of the rectilinear portion of the running path.

The drive may also be configured to bring the ball into a defined state when the cuvette is filled.

A defined state of the ball during the filling of the cuvette is desirable because there is a risk of air bubbles if the liquid, when entering the cuvette, firstly strikes the ball. In order to avoid this, the ball may be brought into a position such that the liquid exiting the filling element does not strike the ball but directly strikes the bottom of the cuvette. The drive may be configured such that it brings the ball into such a position and keeps said ball there. Preferably, said position is an off-center position in the cuvette, more preferably a position at one end of the running rail.

It is alternatively possible for the drive to keep the ball in motion, while the liquid is being introduced into the cuvette. Air bubbles which form are then directly destroyed again as a result of the movement of the ball. The wording that the ball is brought into a defined state by the drive encompasses both the first variant, in which the ball is brought into a fixed position in which it is not struck by the liquid, and the second variant, in which the ball is kept in motion during the filling.

A system of said type has its own inventive content even without the cuvette being provided with a running rail.

In one preferred embodiment, the drive comprises a magnet which is moved on a circular path. The ball can follow the movement of the magnet only in the direction predefined by the running rail. The circular movement of the magnet is therefore converted into a linear movement of the ball. It consequently becomes possible for the ball to be driven for example by way of a simple stepper motor. A measurement device with a drive of this type has its own inventive content even without the ball being brought into a defined state during the filling and without the running rail being formed by projections in the side wall of the cuvette. The concept of the invention can be realized with any type of linear running rail.

The circular path on which the magnet moves may be arranged in the horizontal plane. The diameter of the circular path preferably substantially corresponds to the diameter of the cuvette in the longitudinal direction. Preferably, the movement of the ball extends over at least 50%, preferably at least 60%, more preferably at least 80% of the length of the running rail. The rotational speed can lie between 0.1 revolutions/second and 17 revolutions/second, preferably between 0.2 revolutions/second and 10 revolutions/second. For the purpose of mixing the liquid, the drive is preferably configured to move the magnet on a corresponding circular path. The drive may also be used for stirring the liquid.

The measurement device may comprise a measurement channel which extends from a light source as far as a light sensor through the cuvette which is arranged in a matching position.

The measurement device may also comprise a controller which is configured to activate the functions of the measurement device in a suitable manner. In particular, the controller may be configured to control the interplay between the filling element and the drive. For this purpose, firstly the drive may be activated such that it brings the ball into the defined state. Subsequently, the filling element may be activated such that a specific quantity of liquid is introduced into the cuvette. After the filling, the ball is preferably completely immersed in the liquid, more preferably the fill level in the cuvette is at least twice the diameter of the ball. Consequently, it becomes possible for the measurement channel, which extends through the liquid, to be arranged above the ball such that the measurement process remains uninfluenced by a movement of the ball. The fill quantity of the liquid may lie for example between 100 µl and 200 µl, preferably less than 180 µl.

The measurement device may furthermore comprise a supply unit which is configured to supply a ball to the cuvette. A sensor which checks the presence of the ball may be provided. The measurement device may comprise a heater in order to heat the liquid in the cuvette. In particular, the heater may be configured to heat the liquid to a temperature of between 35° C. and 40° C. The heater may be configured such that the heating of the quantity of liquid extends over a time period of between 1 minute and 3 minutes.

The measurement device may comprise a plurality of measurement stations, thus allowing multiple samples to be examined at the same time. Preferably, each measurement station comprises a drive and a measurement channel. It is possible for use to be made of a cuvette arrangement in which multiple cuvettes are connected to one another such that each measurement channel extends through one cuvette. If the distance between the measurement channels is twice the distance between two adjacent cuvettes of the cuvette arrangement, two measurement runs may be carried out with the cuvette arrangement. In the first measurement run, every second cuvette is examined. Subsequently, the cuvette arrangement is displaced by the length of a cuvette, with the result that the measurement channels extend through the adjacent cannula, which was unused in the first measurement run.

The measurement device may be used in particular with the aim of examining platelet reaction in whole blood or in blood plasma. The procedure is as follows. Firstly, a cuvette is inserted into the measurement device and a ball is introduced into the cuvette. The cuvette is positioned such that the drive is able to act on the ball. The ball is brought into a defined state. The whole blood or the blood plasma is introduced into the cuvette. The blood or blood plasma is heated. During the heating, the ball is preferably stationary. A reagent is added. The ball is set in motion by way of the drive in order to mix the liquid in the cuvette. The light passing through the liquid is measured.

When performing the measurement, it normally emerges that, as a result of an agglomeration of the platelets, the turbidity decreases during the measurement period, that is to say more and more light is able to pass through the liquid. The profile of the light intensity with respect to time may be recorded. A measurement may extend for example over a time period of between 10 minutes and 15 minutes. Conclusions concerning the state of the blood or blood plasma can be drawn from the recording. Preferably, the measurement device comprises five measurement stations so that the blood of a patient can be examined using five different reagents at the same time. If use is made of an arrangement composed of ten cuvettes, then the examination in question can be carried out successively for two different patients by way of the same cuvette arrangement.

The platelets in the blood or blood plasma react sensitively to deviations in the measurement procedure. The measurement device is therefore preferably set up such that the entire measurement procedure is realized fully automatically in order to avoid deviations owing to human interventions. For this purpose, the measurement device may have a receptacle into which the sample is introduced. Preferably, the sample is not moved for a certain time so that the blood or blood plasma can come to rest. Afterwards, for slight mixing of the whole blood, the receptacle may be rotated once or multiple times slowly. In the case of blood plasma, the rotation is preferably omitted. Use may be made of a needle to penetrate into the sample in order to take a specific quantity of the liquid. The liquid may be introduced into the cuvette in order, there, to be examined according to the described procedure. For reproducibility, it is of particular importance here that the ball moves on the running rail because the region in which a large pressure is exerted locally by the ball is thereby kept small. The uniform spacing between the ball and the side surfaces and also the bottom surfaces of the cuvette, as a result of which it is achieved that the shearing in the liquid which occurs during mixing is as uniform as possible, is also important. Furthermore, it emerges from the form according to the invention of the cuvette that the measurement is possible with the very small quantity of liquid of approximately 150 µl. By contrast, approximately 300 µl to 400 µl of the liquid is required in the case of conventional measurements. Particularly for samples which come from children, it is often the case that there is not so much liquid available.

The invention also relates to a method for examining a liquid, in particular blood or blood plasma, in which light is directed through a quantity of the liquid, which quantity is arranged in a cuvette, and the light passing through the liquid is recorded. The method can be carried out through the use of a cuvette according to the invention and/or a measurement device according to the invention. The method can be developed by features which are described in connection with the cuvette according to the invention and/or in connection with the measurement device according to the invention.

BRIEF DESCRIPTION OF THE DRAWINGS

The invention will be described by way of example below with reference to the appended drawings on the basis of advantageous embodiments. In the drawings.

DETAILED DESCRIPTION

Figure 1A:
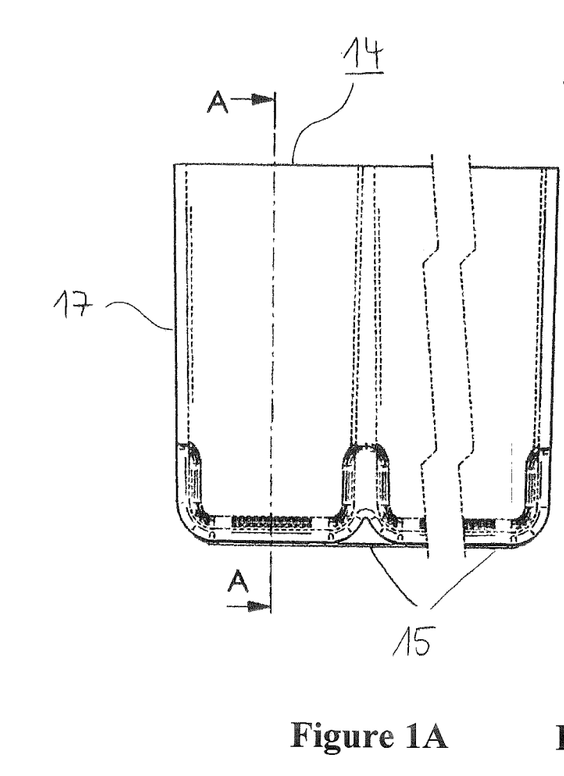
FIGS. 1A-1D show various views of a cuvette arrangement according to the invention.
Figure 1B:
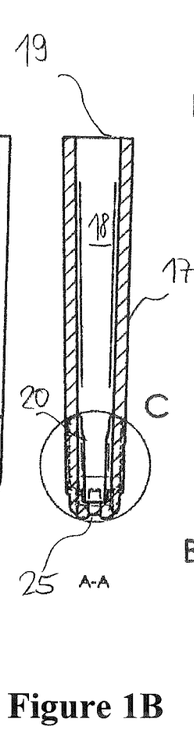
Figures 1C, 1D:
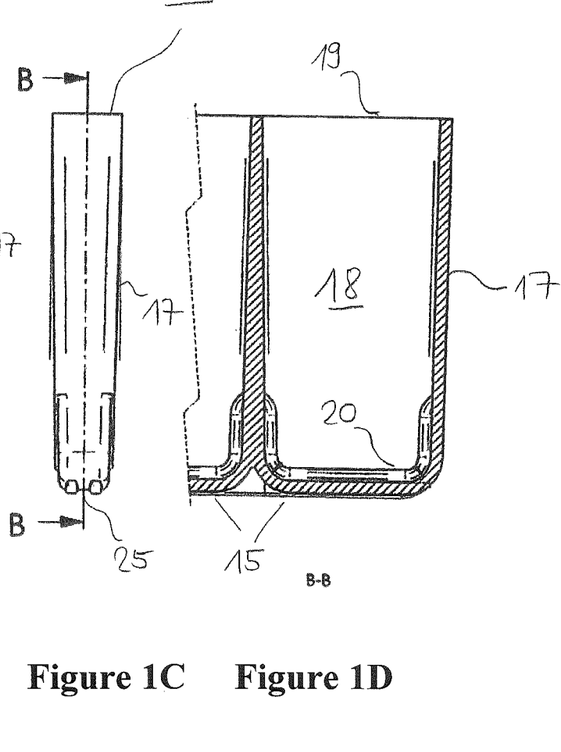

A cuvette 14 according to the invention is shown as part of a cuvette arrangement 15 according to the invention in plan view in FIGS. 1A and 1C, and as a sectional illustration in FIGS. 1B and 1D. A cuvette 14 comprises an inner space 18 which is surrounded by a cuvette housing 17 and which is in contact with the surroundings via an inlet 19. A running rail 20 which is connected to the cuvette housing 17 extends in a lower region of the inner space 18.

In this embodiment, the running rail 20 is curved upward at both ends and follows the profile of the cuvette housing 17. Moreover, the inner space 18 is slightly widened from the bottom upward. The cuvette housing 17 also has, on a lower outer side, a guiding device 25 which extends over all the cuvettes 14 of a cuvette arrangement 15.

Figure 2A:
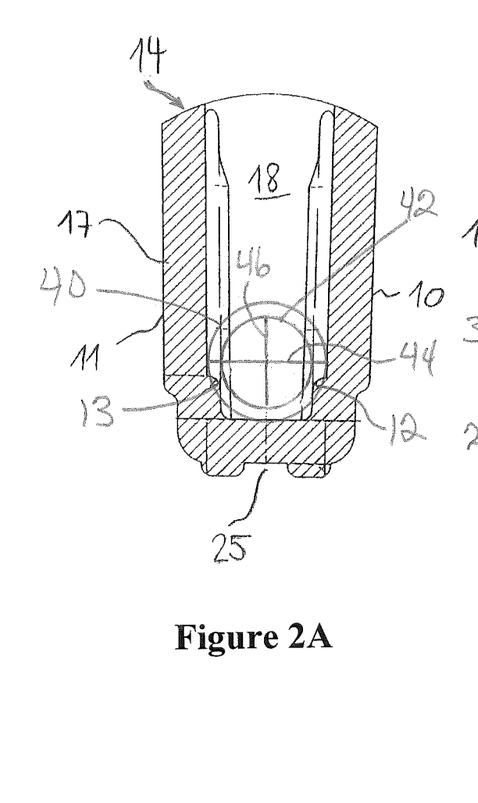
FIG. 2A shows an enlarged sectional illustration of parts of a cuvette from FIGS. 1A-1D.
Figure 2B:
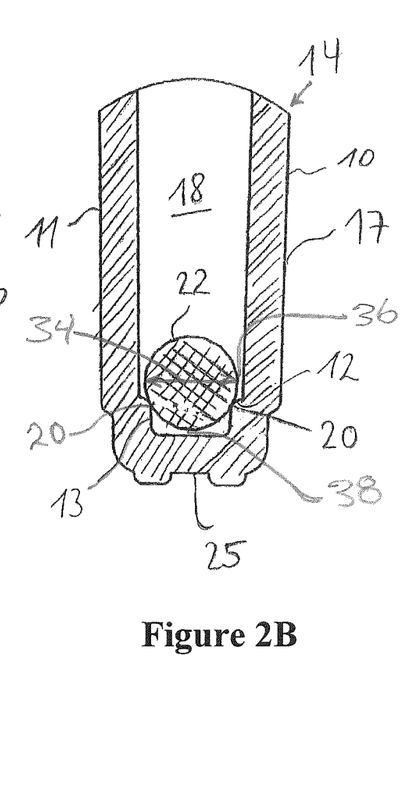
FIG. 2B shows an enlarged sectional illustration of the cuvette from FIG. 2A with a ball.

The enlarged illustrations in FIGS. 2A and 2B show the lower part of a cuvette 14 according to the invention. As is shown in FIG. 2A, the running rail 20 extends within the inner space 18 along a lower side of the cuvette housing 17 and runs further along a rounded edge and a further side of the cuvette housing 17. In FIG. 2B, a ball 22 having a defined diameter 34 is arranged in the inner space 18 such that the ball 22 bears on the running rail 20. Here, with the exception of the illustrated bearing points (contact region) on the running rail 20, the ball 22 is not in contact with the cuvette housing 17. The distance 38 between the lowermost point of the ball 22 and the cuvette housing 17 is identical to the distance 36 between the points of the ball 22 which are located farthest to the side and the side wall of the cuvette housing 17.

The curvature at the ends of the running rail 20 ensures that the ball 22 cannot run against the end wall of the cuvette. If the ball 22 moves at high speed along the running rail 20, it can run upward at the ends and is thus slowed down before it comes into contact with the cuvette housing 17.

It can be seen in FIG. 2B that an imaginary first circle 40 the diameter 44 of which is slightly larger than the diameter 34 of the ball 22 intersects the two projections 12, 13 of the running rail 20. By contrast, an imaginary second circle 42 the diameter 46 of which is slightly smaller than the diameter 34 of the ball 22 does not intersect the two projections.

Figure 3:
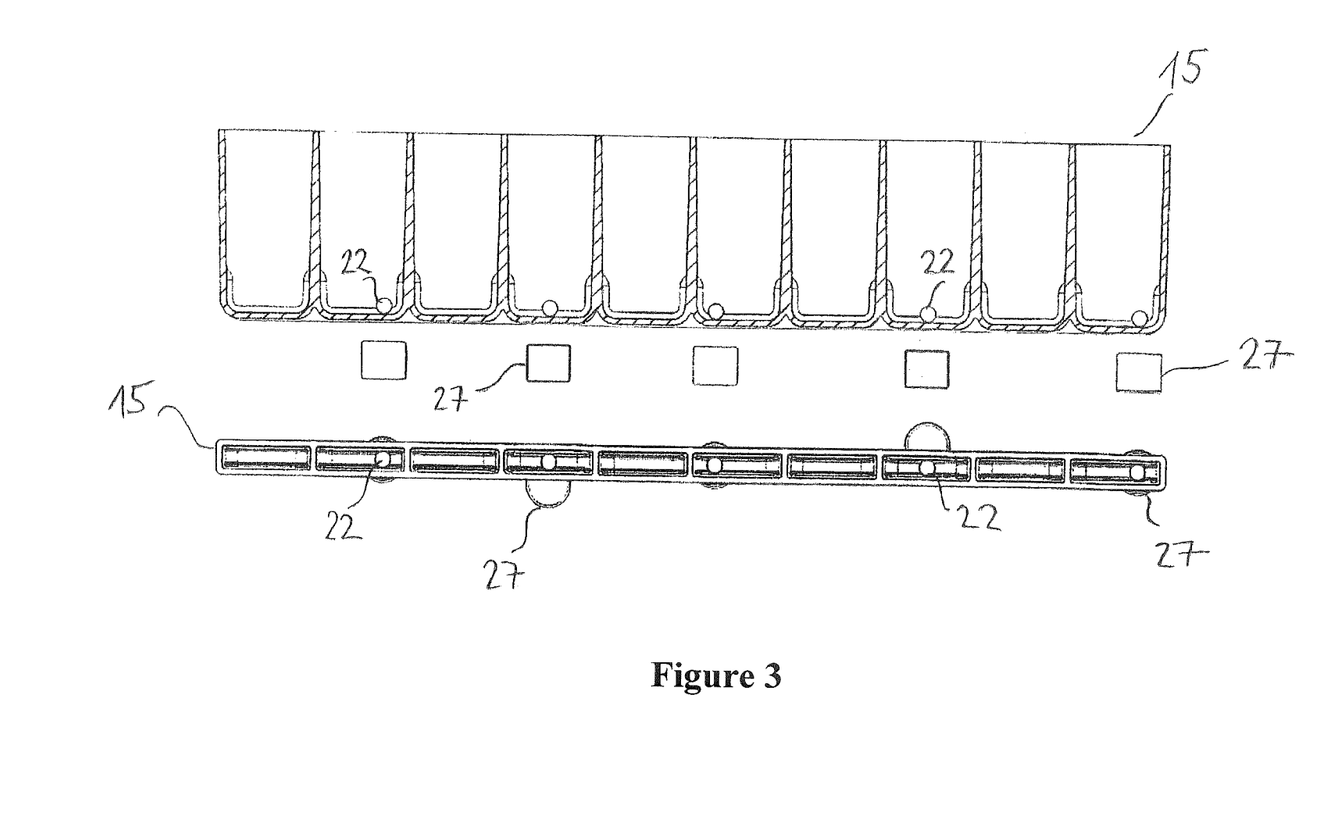
FIG. 3 shows, in a view from the side and a view from above, a schematic illustration of a measurement device according to the invention.

FIG. 3 shows a cuvette arrangement 15 consisting of ten cuvettes 14, wherein the running rails 20 of the individual cuvettes 14 are arranged in a row. A ball 22 is arranged in every second cuvette 14. The position of the balls 22 results from the magnets 27 which are arranged in each case outside the cuvette housing 17 and which interact with the ferromagnetic balls 22.

As a result of the magnetic interaction, it is possible to keep the ball 22 in a defined state, for example at one end of the running rail 20. Such a defined state of the ball 22 is particularly advantageous when introducing a liquid into the inner space 18 (not shown) by way of a filling element (not shown). In this way, it is possible to avoid the situation in which a pipetting jet strikes the ball 22 directly and unnecessary turbulence is thereby generated in the liquid. It is additionally possible that the ball 22 is in a defined state in that it moves slowly or at constant speed along the running rail 20, as is explained in connection with the method according to the invention.

The method according to the invention for stirring a liquid in a cuvette can be understood on the basis of the illustrated states of the balls 22 and the magnets 27. The cuvette arrangement 15, with balls 22 and magnets 27, is shown from the side in the upper part of FIG. 3, while the same state can be seen in a bird's eye view in the lower part of FIG. 3. In this embodiment, the magnet 27 is illustrated in the form of a cylinder which has a rectangular cross section as viewed from the side, and a circular cross section as viewed from above.

During a full revolution according to the method according to the invention, the magnet 27 moves once along a circular path, while the ball 22 moves once back and forth along the running rail 20. If the states in this exemplary illustration are considered from left to right, then the ball 22 is initially arranged on the right side of the running rail 20, while the magnet 27 is placed directly underneath the ball 22 below the right side of the running rail 20. If the magnet 27 moves along one quarter of a circular path in a clockwise direction, the ferromagnetic ball 22 rolls as far as the center of the running rail 20, and rolls further as far as the left-hand edge of the running rail 20 when the magnet 27 has covered the second quarter on the circular path. The return path is realized analogously until both the magnet 27 and the ferromagnetic ball 22 have again reached their starting positions.

The magnet 27 can be driven in steps by a stepper motor (not shown), and the ball 22 can be partially or completely immersed in a sample (not shown). The repeated movement of the ferromagnetic ball 22 then generates a pumping action in the sample, which ensures that the sample is efficiently mixed.

Figure 4:
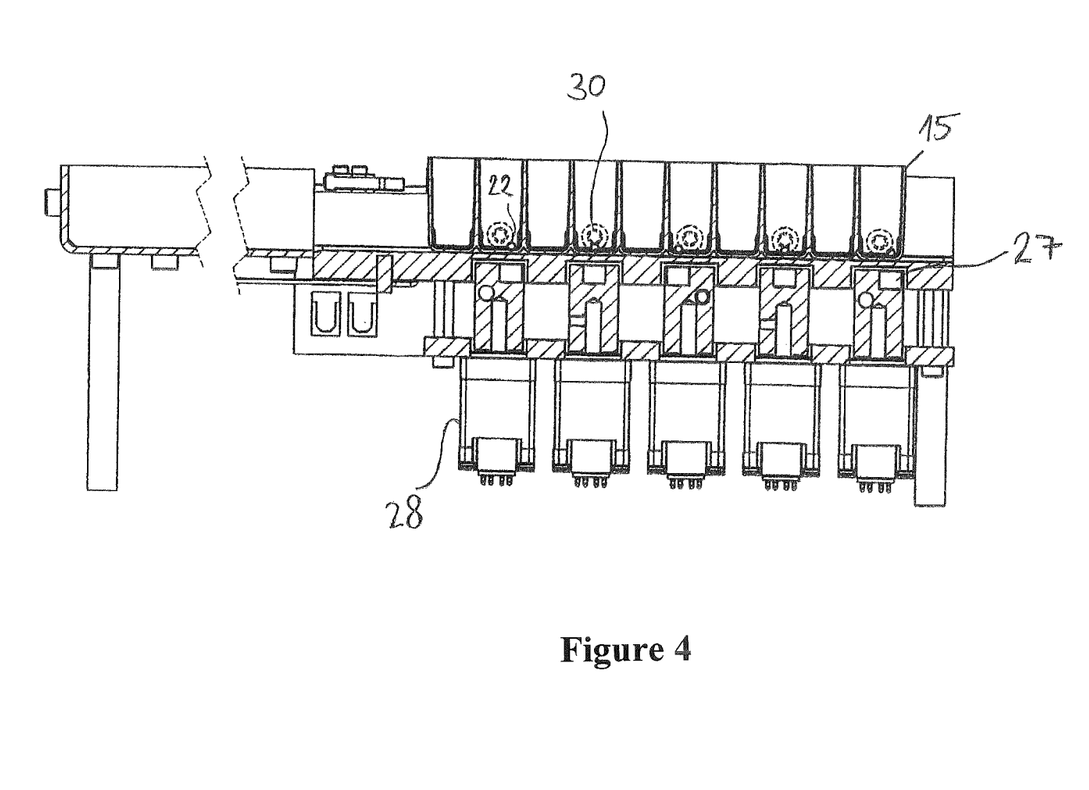
FIG. 4 shows a schematic illustration of a measurement device according to the invention for carrying out an optical measurement at the liquid.
Figure 5:
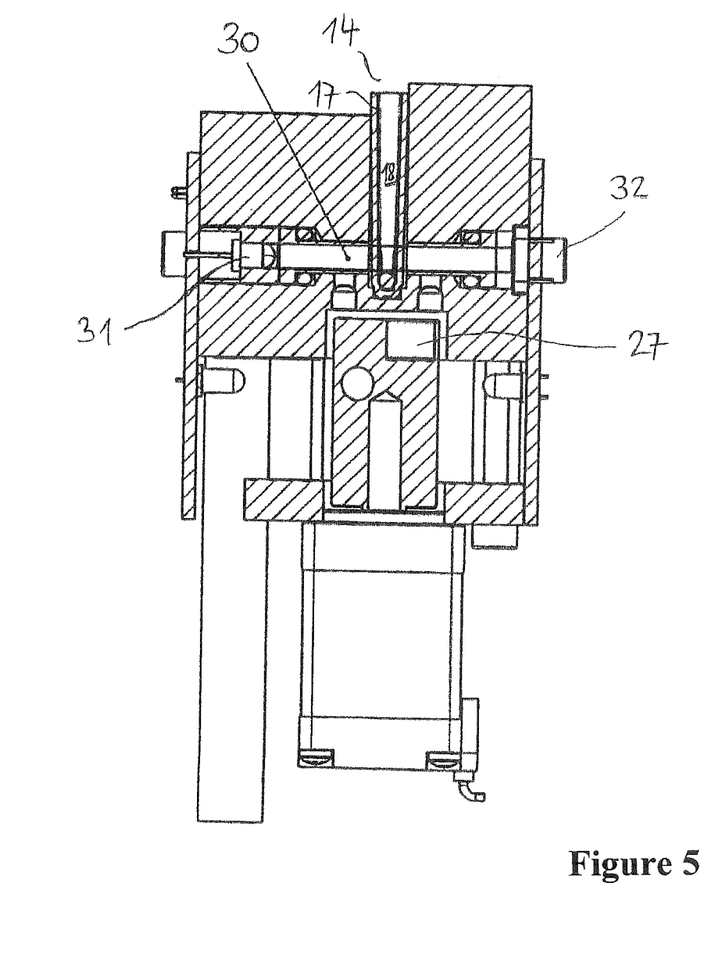
FIG. 5 shows a side view of the measurement device from FIG. 4.

FIGS. 4 and 5 show a machine according to the invention for determining the turbidity of a liquid, which machine is configured to carry out the method according to the invention and to be filled with a cuvette arrangement 15 according to the invention. As shown in FIG. 3, the cuvette arrangement 15 has a ball 22 in every second cuvette. The arrangement of the balls 22 and the alignment of the magnets 27 situated therebelow is identical overall to the example from FIG. 3. The guiding device 25 of the cuvette arrangement 15 interacts with the machine such that the cuvette arrangement is able to be displaced horizontally and is able to be aligned according to the magnets 27. In addition, five stepper motors 28, which are arranged in a row and are able to be activated separately, form part of the machine according to the invention in this embodiment. The stepper motors 28 are configured to move in each case one magnet 27 along a circular path. Consequently, simultaneous stirring in five cuvettes is possible at the same time.

The machine according to the invention allows the turbidity of a sample to be determined fully automatically during the stirring or after the stirring has ended. A measurement channel 30 which extends through the cuvette 14 is provided for this purpose. The measurement channel 30 is preferably arranged such that it extends centrally and at a height at which the inner space 18 is completely filled with a sample. During the measurement, the ball 22 should thus be arranged, or moved, in a region which does not cover the measurement channel 30.

A side sectional illustration of the machine according to the invention for determining the turbidity of a liquid is shown in FIG. 5. The measurement channel 30 extends between a light source 31 and a photodetector 32 such that the light passes through the cuvette 14 in a region above the ball 22. Light emitted from the light source 31 passes through the cuvette housing 17 into the inner space 18 of the cuvette 14, is transmitted through the sample, and passes once more through the cuvette housing 17 out of the cuvette 14 in order finally to be recorded by a photodetector 32.

The inner space 18 should have a small extent in the region of the measurement channel 30 in order that the light is not completely absorbed by the sample. In order not to distort the measurement results, a wall thickness of 2 mm should not be exceeded by the cuvette housing 17 in the region of the measurement channel 30. The measurement channel 30 should also be sufficiently large in order to cover a representative region of the sample.

The machine according to the invention allows measurement of the turbidity of a sample, or different samples in five measurement channels 30 simultaneously. At the end of the measurement, it is possible for the cuvette arrangement 15 to be displaced horizontally, for example by one cuvette position, in order to align the five hitherto unused cuvettes 14 according to the stepper motors 28 and measurement channels 30, and to repeat the stirring according to the method according to the invention and the measurement of the turbidity.

The invention claimed is:

1. A cuvette for stirring a liquid, said cuvette comprising:
a housing (17) having side walls (10, 11) and end walls defining an inner space (18) for receiving the liquid, said housing (17) extending from a closed first end to an inlet (19); and
a running rail (20) formed by two projections (12, 13) projecting into a lower region of said inner space (18) from said side walls (10, 11), said running rail (20) for guiding movement of a ball (22) in said inner space (18),
wherein said running rail (20) follows a profile of the housing from a bottom of the cuvette to at least one of the side walls and extends along the side walls toward said inlet, and wherein said running rail (20) has a rectilinear portion enabling movement of the ball along said rectilinear portion and wherein said running rail is deflected toward said inlet (19) at both ends to prevent the ball from striking an end wall of the cuvette such that the ball can move parallel to the side walls toward said inlet.

2. The cuvette of claim 1, wherein an imaginary first circle (40), which is perpendicular to the running rail (20) and which touches the bottom of the inner space (18) and the side walls (10, 11) of the inner space (18), intersects the two projections (12, 13), while a smaller, concentric imaginary second circle (42) does not intersect the projections (12, 13), wherein the diameter (46) of the second circle (42) is at least 50 % of the diameter (44) of the first circle (40).

3. The cuvette of claim 1, wherein said projections (12, 13) have a convex cross sectional shape where the projections (12, 13) are adapted to contact the ball (22).

4. The cuvette of claim 1, wherein the side walls (10, 11) of the cuvette (14) are substantially parallel to one another.

5. The cuvette of claim 1, wherein said side walls (10, 11) define an included angle of between 0.2° and 5°, preferably of between 0.5° and 2°, in a direction facing said inlet (19).

6. The cuvette of claim 1, wherein a distance between an outer side of the first side wall (10) and an outer side of the second side wall (11) at a location of a measurement channel 30 is less than 8 mm.

7. A system composed of a cuvette (14) of claim 1 and of a ball (22), wherein the ball (22) bearing on the running rail (20) is spaced apart from the bottom surface of the cuvette (14) by a distance (38) which differs by no more than 50% from the distance (36) from the side wall (10, 11).

8. A system composed of a measurement device and of a cuvette (14) of claim 1, wherein the measurement device comprises:
   a. a filling element which is configured to introduce a quantity of liquid into the cuvette (14);
   b. a drive (28) for a ball (22) arranged in the cuvette (14), wherein the drive (28) is configured to bring the ball (22) into a defined state during introduction of liquid into the cuvette (14), wherein bringing the ball (22) into a defined state comprises:
   moving said ball (22) to a position where liquid entering the cuvette does not strike the ball (22).

9. A system composed of a measurement device and of a cuvette (14) of claim 1, wherein the measurement device comprises:
   a. a filling element which is configured to introduce a quantity of liquid into the cuvette (14);
   b. a drive (28) for a ball (22) arranged in the cuvette (14), wherein the drive (28) is configured to bring the ball (22) into a defined state during introduction of liquid into the cuvette (14), wherein, in the defined state, the ball (22) is kept in motion, wherein the drive (28) comprises a magnet (27) which is moved on a circular path.

10. The system of claim 8, wherein the measurement device comprises a measurement channel (30) which extends from a light source (31) as far as a light sensor (32) and which extends through the cuvette (14) above the ball (22) bearing on the running rail (20).

11. The system of claim 8, wherein the measurement device comprises a plurality of measurement stations, wherein each of the plurality of measurement stations has a measurement channel (31, 32) and a drive (28).

12. A method for examining a liquid, said method comprising:
   providing a cuvette comprising a housing (17) having side walls (10, 11) and end walls defining an inner space (18) for receiving the liquid, said housing (17) extending from a closed first end to an inlet (19); and a running rail (20) formed by two projections (12, 13) projecting into a lower region of said inner space (18) from said side walls (10, 11), said running rail (20) for guiding movement of a ball (22) in said inner space (18), wherein said running rail (20) follows a profile of the housing from a bottom of the cuvette to at least one of the side walls and extends along the side walls toward said inlet, said running rail (20) having a rectilinear portion enabling movement of the ball along said rectilinear portion and wherein said running rail is deflected toward said inlet (19) at both ends to prevent the ball from striking an end wall of the cuvette such that the ball can move parallel to the side walls toward said inlet;
   providing the ball in said inner space (18) movement of which is guided by said running rail such that the movement of the ball is deflected upward at, at least one of, the ends of the running rail;
   introducing a liquid to be examined into said cuvette;
   directing a light beam through the liquid arranged in said cuvette; and
   measuring the portion of light passing through the liquid.

13. The method of claim 12, wherein said step of introducing a liquid comprises:
   bringing the ball (22) into a defined state during introduction of liquid into the cuvette (14),
   wherein bringing the ball (22) into a defined state comprises:
   moving said ball (22) to a position where liquid entering the cuvette does not strike the ball (22); or
   keeping said ball in motion while the liquid is being introduced to the cuvette.

14. The method of claim 12, wherein said step of providing a ball comprises:
   providing a ball made of magnetic material; and
   using a magnet (27) to move said ball within said cuvette.

* * * * *